(12) United States Patent
Ives et al.

(10) Patent No.: US 6,198,958 B1
(45) Date of Patent: Mar. 6, 2001

(54) METHOD AND APPARATUS FOR MONITORING A MAGNETIC RESONANCE IMAGE DURING TRANSCRANIAL MAGNETIC STIMULATION

(75) Inventors: John R. Ives, Lexington; Alvaro Pascual-Leone, Wayland; Qun Chen, Brookline, all of MA (US)

(73) Assignee: Beth Israel Deaconess Medical Center, Inc.

( * ) Notice: Subject to any disclaimer, the term of this patent is extended or adjusted under 35 U.S.C. 154(b) by 0 days.

(21) Appl. No.: 09/096,725

(22) Filed: Jun. 11, 1998

(51) Int. Cl.[7] .................................................. A61B 5/05
(52) U.S. Cl. ........................ 600/411; 600/544; 600/13
(58) Field of Search .................................. 600/411, 544, 600/13, 14

(56) References Cited

U.S. PATENT DOCUMENTS

| | | | |
|---|---|---|---|
| 4,033,334 | 7/1977 | Fletcher et al. | 128/2.1 E |
| 4,736,751 | * 4/1988 | Gevins et al. | |
| 4,949,725 | 8/1990 | Raviv et al. | 128/731 |
| 4,951,674 | 8/1990 | Zanakis et al. | 128/653 R |
| 4,974,602 | 12/1990 | Abraham-Fuchs et al. | 128/731 |
| 4,994,015 | * 2/1991 | Cadwell | |
| 5,119,816 | 6/1992 | Gevins | 128/644 |
| 5,159,929 | 11/1992 | Morris et al. | 128/653.2 |
| 5,217,010 | 6/1993 | Tsitlik et al. | 128/419 PG |

(List continued on next page.)

FOREIGN PATENT DOCUMENTS

| | | | |
|---|---|---|---|
| 28 31 099 | 1/1980 | (DE) | A61B/5/04 |
| 2 307 411 | 5/1998 | (GB) | A61B/5/04 |
| WO 92/21281 | 12/1992 | (WO) | A61B/5/00 |
| WO 94/12099 | 6/1994 | (WO) | A61B/5/04 |
| WO 98/18384 | 5/1998 | (WO) | A61B/5/04 |

OTHER PUBLICATIONS

International Search Report from International Patent Application PCT/US99/08489, filed Apr. 22, 1999.

International Search Report from International Patent Application PCT/US99/13051, filed Jun. 9, 1999.

Ilmoniemi RJ, Virtanen J: "Neuronal reposnses to magnetic stimulation reveal cortical reactivity and connectivity", NeuroReport, vol. 8, No. 16, Nov. 10, 1997, pp. 3537–3540.

Ruohonen J: "Transcranical Magnetic Stimulation: Modelling and New Techniques" Dissertation, Department of Engineering Physics and Mathematics Laboratory of Biomedical Engineering Helsinki University of Technology, Dec. 4, 1998, p. 28, paragraph 2; p. 30, paragraph 1; figure 6.

Bohning, D: "Interleaved Transcranial Magnetic Stimulation (TMS) and fMRI", proceedings of the international society for magnetic resonance in medicine, Sixth Scientific Meeting and Exhibition, Sydney, Australia Apr. 18–24, 1998, vol. 1. p. 508.

Bohning, D: "Echoplanar Bold fMRI of Brain Activation Induced by Concurrent Transcranial Magnetic Stimulation", Investigative Radiology, vol. 33, No. 6, Jun 1998, pp 336–340.

(List continued on next page.)

Primary Examiner—Marvin M. Lateef
Assistant Examiner—Shawna J Shaw
(74) Attorney, Agent, or Firm—Wolf, Greenfield & Sacks, P.C.

(57) ABSTRACT

A method and apparatus for monitoring a magnetic resonance image of a patient during administration of transcranial magnetic stimulation. The method includes the steps of applying transcranial magnetic stimulation (TMS) to a patient using a probe that is substantially constructed of non-ferromagnetic material, monitoring a magnetic resonance image (MRI) of the patient during TMS wherein application of the TMS does not need to by synchronized to monitoring of the MRI.

17 Claims, 2 Drawing Sheets

U.S. PATENT DOCUMENTS

| | | | |
|---|---|---|---|
| 5,220,921 | 6/1993 | Ferris et al. | 128/653.1 |
| 5,269,315 | 12/1993 | Leuchter et al. | 128/731 |
| 5,323,776 | 6/1994 | Blakeley et al. | 128/633 |
| 5,455,162 | 8/1995 | Ives . | |
| 5,707,334 | 1/1998 | Young | 600/9 |
| 5,769,778 * | 6/1998 | Abrams et al. . | |
| 5,794,620 * | 8/1998 | Dossel et al. . | |
| 5,833,600 * | 11/1998 | Young . | |

OTHER PUBLICATIONS

Bohning, D: "Mapping transcranial magnetic stimulation (TMS) fields in vivo with MRI", Neuroreport, vol. 8, No. 11, 1997, pp. 2535–2538.

Pascual–Leone, A, et al.: "Effects of Repetitive Transcranial Magnetic Stimulation (rTMS) on Motor Cortex Activity During a Rate Controlled Motor Task as Measured by Functional Magnetic Resonance Imaging (fMRI)", Neurology, vol. 48, No. 3, (supp. 2), 1997, p. A106.

* cited by examiner

METHOD AND APPARATUS FOR MONITORING A MAGNETIC RESONANCE IMAGE DURING TRANSCRANIAL MAGNETIC STIMULATION

BACKGROUND OF THE INVENTION

1. Field of the Invention

The present invention relates to medical diagnostic and treatment methods and apparatus.

2. Discussion of the Related Art

Transcranial magnetic stimulation (TMS) is a technique for stimulating the human brain non-invasively. TMS uses the principle of inductance to get electrical energy across the scalp and skull without the pain of direct percutaneous electrical stimulation. It involves placing a coil of wire on the scalp and passing a powerful and rapidly changing current through it. This produces a magnetic field which passes unimpeded and relatively painlessly through the tissues of the head. The peak strength of the magnetic field is related to the magnitude of the current and the number of turns of wire in the coil. This magnetic field, in turn, induces a much weaker electrical current in the brain. The strength of the induced current is a function of the rate of change of the magnetic field, which is determined by the rate of change of the current in the coil. In order to induce enough current to depolarize neurons in the brain, the current passed through the stimulating coil must start and stop or reverse its direction within a few hundred microseconds.

TMS is currently used in several different forms. In a first form, called single-pulse TMS, a single pulse of magnetic energy is delivered from the coil to the patient. Repetitive TMS or rTMS, refers to the delivery of a train of pulses delivered over a particular time period. An example of rTMS could be a train of pulses having a 10 Hz repetition rate that lasts for approximately 8 to 10 seconds. In a typical application, this train of pulses is repeated every 30 seconds for up to 20 or 30 minutes.

Magnetic resonance imaging (MRI) is a technique for non-invasive imaging and diagnosis of body organs that uses the interaction between a magnetic field and protons in the body to provide images of body tissues. Functional MRI or fMRI is a subset of this technology and produces images of activated brain regions by detecting the indirect effects of neural activity on local blood volume, flow, and oxygen saturation. MRI systems have been commercially available for a number of years.

The inventors have realized that it would be desirable to combine TMS and MRI technologies in order to provide diagnostic and therapeutic benefits.

Conventionally, however, these two technologies have not been combined for a variety of reasons. First, it has been thought that there may be interactions between the TMS equipment and the MRI equipment due to the fact that both types of equipment generate and use magnetic fields. Therefore, the instantaneous magnetic field associated with the discharge of the TMS coil, which may be on the order of more than two TESLA might interact with the 1.5 TESLA static magnetic field of the MRI system in some unpredictable manner. Second, the discharge of the TMS coil near the sensitive imaging coil of the MRI system might disable or destroy the receiving circuitry within the imaging coil. Third, the mere presence of the TMS coil near the patient's head might contribute artifacts into any images provided by the MRI system. Fourth, the TMS electronics alone might produce artifacts on the images produced by the MRI system.

SUMMARY OF THE INVENTION

In broad terms, one aspect of the present invention provides a method and apparatus for monitoring a patient's MRI during TMS that does not require a time synchronization of the operation of the TMS device and the MRI system.

This aspect of the invention is provided by a method and apparatus for monitoring a magnetic resonance image of a patient during administration of transcranial magnetic stimulation, including a transcranial magnetic stimulation (TMS) device and a magnetic resonance imaging (MRI) system. The system also includes a probe, coupled to the TMS device, the probe being constructed and arranged to deliver transcranial magnetic stimulation, wherein the probe is substantially constructed of non-ferromagnetic material, wherein timing of operation of a TMS device does not need to be synchronized to timing of operation of the MRI system.

In accordance with another aspect of the invention, a probe is provided for delivering the magnetic pulse provided by a transcranial stimulation (TMS) device to a patient wherein the probe is substantially constructed of non-ferromagnetic material.

Within this disclosure the term transcranial magnetic stimulation (TMS) is meant to include both single-pulse TMS and repetitive TMS. With this disclosure, the term magnetic resonance imaging (MRI) is meant to include all types of MRI and functional MRI.

BRIEF DESCRIPTION OF THE DRAWINGS

In the drawings, which are incorporated herein by reference and in which like elements have been given like reference characters.

DETAILED DESCRIPTION

Figure 1:
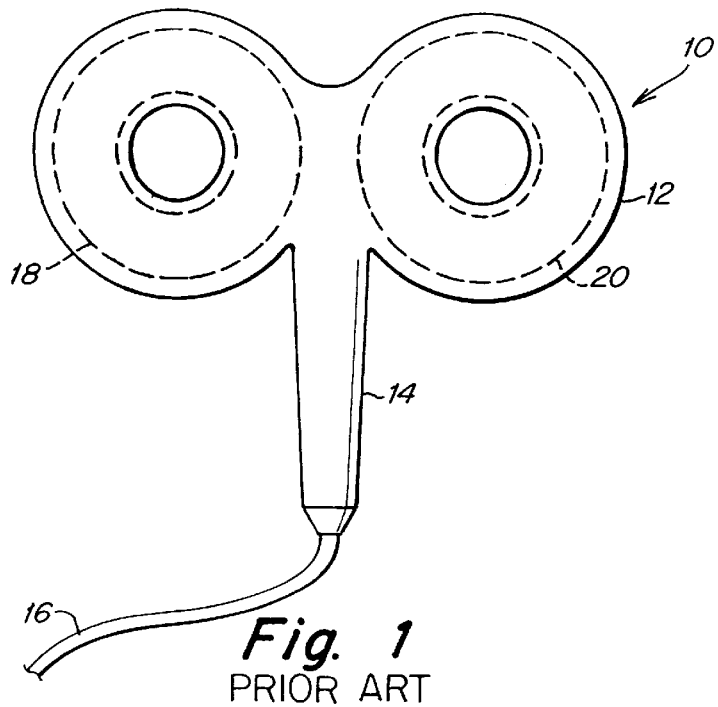
FIG. 1 is a plane view of a conventional TMS probe.

FIG. 1 illustrates a typical TMS probe 10. The probe includes a housing 12, typically constructed of molded plastic, having a handle region 14. Conductor 16 is coupled from a TMS device to handle region 14. Typically, probe 10 is held within close proximity to the patient's head in a region where magnetic stimulation is desired. The operator typically holds probe 10 by using handle region 14.

Within probe 10 are two coils 18, 20 typically constructed of copper. When a high current short time duration signal is provided to coils 18, 20 via conductor 16, a large magnetic pulse is generated. Coils 18 and 20 are constructed and arranged so that the magnetic pulse provided by each coil constructively combines to deliver a magnetic pulse wave.

In monitoring an MRI during TMS, the inventors discovered that using a probe such as probe 10 presented two main problems. First, the shape of probe 10 with handle region 14 protruding from the region of the junction between coils 18 and 20 makes the probe bulky and difficult to insert into the imaging coil of an MRI system. In addition, the inventors discovered that when the probe was located in the imaging coil of an MRI system, significant distortion of the MRI image as well as voids in the MRI image occurred, due to the significant amount of ferromagnetic material incorporated into probe 10. This ferromagnetic material came primarily from various epoxies used to hold the probe together and to hold coils 18, 20 in position, as well as various metal interconnects used to connect coils 18 and 20 to conductor 16.

Figure 2:
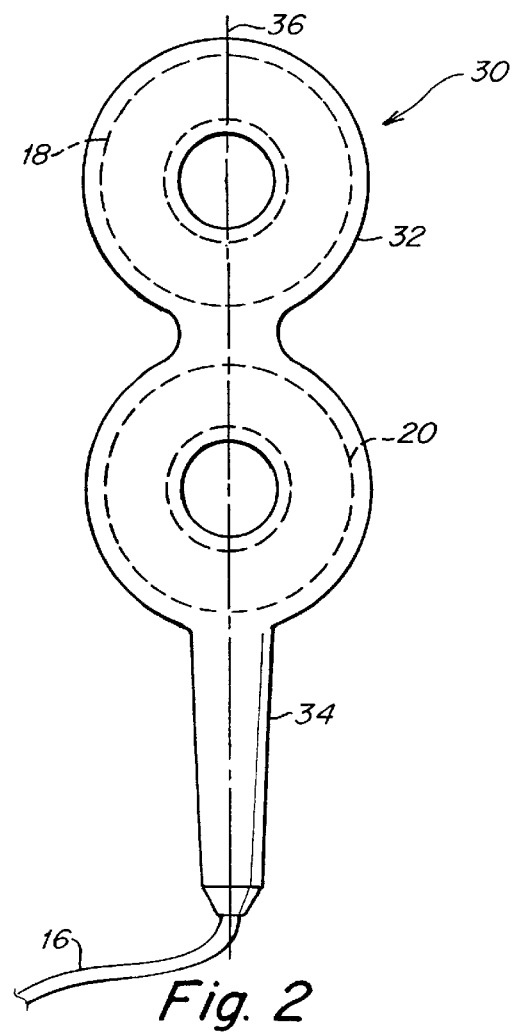
FIG. 2 is a plane view of a TMS probe in accordance with one aspect of the invention.

To overcome the deficiencies of probe 10, the probe of FIG. 2 was developed. As illustrated in FIG. 2, probe 30 includes a housing 32 that may be constructed of plastic or a suitable material similar to housing 12. However, unlike probe 10, probe 30 has a handle region 34 that is disposed away from the intersection of coils 18, 20. In one embodiment, handle region 34 is disposed in line with axis 36 so that handle region 34, coil 18, and coil 20 are substantially in line.

The purpose of locating coil 18, coil 20, and handle region 34 substantially in line is that this configuration is easier to place inside the imaging coil of the MRI system. In the MRI system, the imaging coil must be located in close proximity to the patient's head and there is a relatively limited amount of space available between the patient's head and the imaging coil. The configuration of FIG. 2 allows the probe to fit within the imaging coil and allows conductor 16 to exit and be connected to the TMS device in a manner that is comfortable for the patient.

A second feature of probe 30 is that substantially all ferromagnetic material including interconnects and epoxies has been removed. Any interconnects necessary between coils 18, 20 and conductor 16 are provided by non-ferromagnetic material such as copper. Probe 30 is thus constructed of substantially non-ferromagnetic materials. The use of non-ferromagnetic materials significantly reduces the magnitude of any distortion in the MRI image introduced by the presence of probe 30 within the imaging coil of the MRI system. Within this disclosure, the term non-ferromagnetic is meant to refer to materials having very low magnetic permeablities and relatively low residual magnetism and hystersis. One example of non-ferromagnetic materials is copper.

Figure 3:
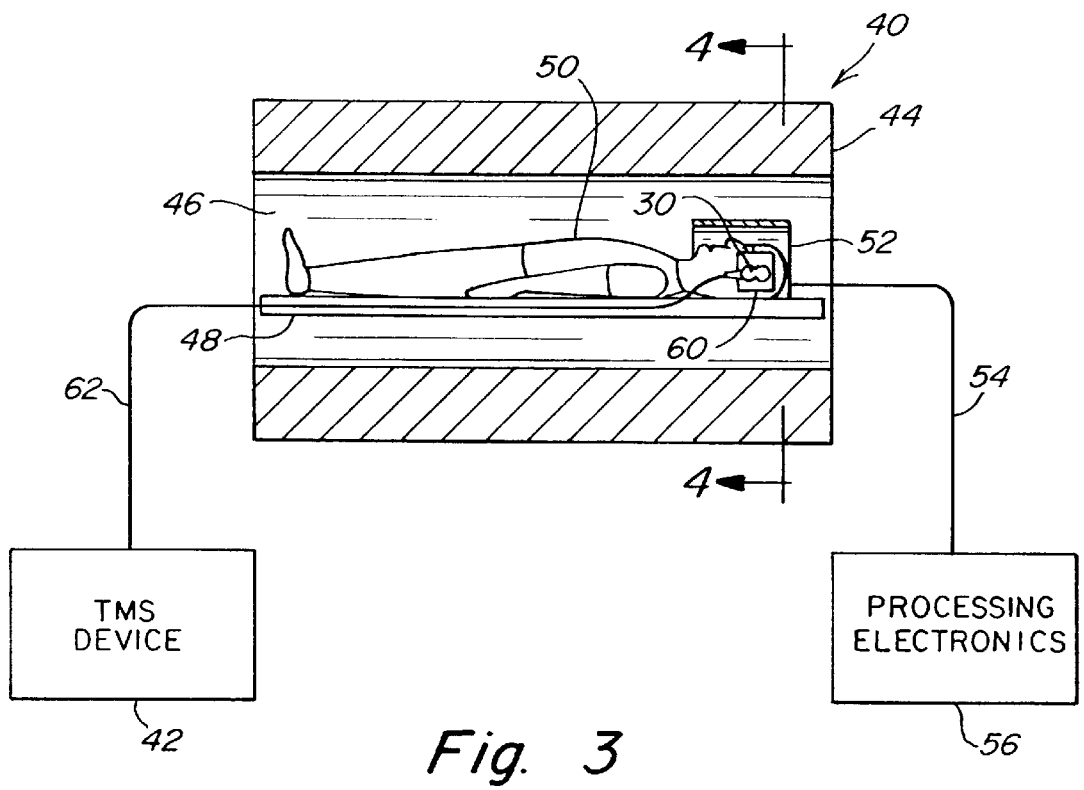
FIG. 3 illustrates a system in accordance with the present invention in which TMS may be used in conjunction with MRI.

Reference is now made to FIG. 3, which figure illustrates how a TMS device can be used in conjunction with an MRI system. In FIG. 3, an MRI system 40 and a TMS device 42 are provided. MRI system 40 may be a Siemens Vision System magnetic resonance imaging system and typically includes a cylindrical magnet 44 having a bore 46 in which a patient 50 is placed in order to undergo magnetic resonance imaging. The MRI system includes a sliding platform 48 that the patient 50 lies on. An imaging coil 52 typically including a number of pickup coils is provided. Imaging coil 52 detects the magnetic field generated as a result of exposure of patient 50 to the large magnetic field provided by magnet 44.

The signal detected by imaging coil 52 is carried by cable 54 to processing electronics 56. Processing electronics 56 process the signals provided by imaging coil 52 to provide a magnetic resonance image of the brain of patient 50.

Figure 4:
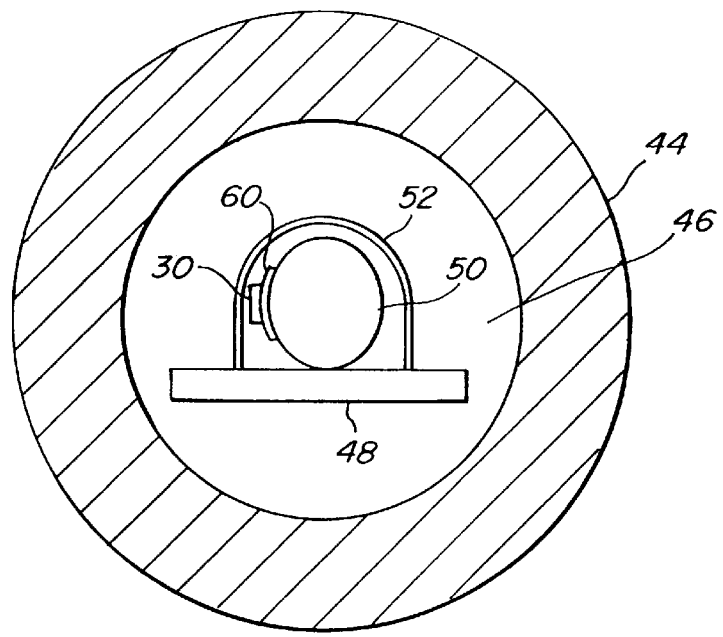
FIG. 4 is a cross section along line 4—4 of FIG. 3 illustrating the placement of various components within the system.

Reference is now made to FIG. 4, which figure is a cross sectional view along lines 4—4 of FIG. 3. In FIG. 4, the relationship among the various components is illustrated. As can be seen in FIG. 4, imaging coil 52 surrounds the head of patient 50 and probe 30 is disposed between imaging coil 52 and the head of patient 50. The inventors have noted from experiments that when probe 30 generates a magnetic pulse, there is some interaction between the static magnetic field provided by magnet 44 and the magnetic pulse provided by probe 30. This interaction may in fact cause probe 30 to actually move or twist. To avoid any injury or discomfort to the patient as a result of this twisting or torquing motion, a pad 60 is disposed between the head of patient 50 and probe 30. In order to maximize the effect of the magnetic pulse provided by probe 30, pad 60 should be as thin as possible while still providing appropriate protection and comfort for patient 50. The inventors have determined that pads having a material thickness in the range of ¼" to ⅓" can make the patient comfortable without significantly diminishing the strength of the magnetic pulse delivered by probe 30.

In their experiments, the inventors found that there were no adverse effects on processing electronics 56 as a result of the magnetic pulse generated by probe 30.

TMS device 42 may be, in one embodiment, a Magstim Super Rapid device. The inventors have determined that as long as the TMS device 42 is kept at least ten feet away from MRI system 40, there are no adverse electromagnetic interactions between MRI system 40 and TMS device 42. Extension cables 62 are used to provide the connection between probe 30 and TMS device 42.

The system illustrated in FIGS. 3 and 4 may be operated in a number of ways. One way is to begin magnetic resonance imaging of a patient and then to apply TMS pulses and observe the effects of the TMS treatment on the MRI. Another way of operating the system is to apply a TMS treatment and then turn off the TMS device 42 and then observe the MRI. Monophasic or biphasic magnetic stimulation may be used as the mode of brain stimulation. Symmetrical biphasic stimulation, in which the pulses are of equal strength is useful because it can reduce the amount of movement of probe 30.

The use of transcranial magnetic stimulation in combination with magnetic resonance imaging can provide a variety of diagnostic, research, and therapeutic benefits.

The invention may be used to create a functional map of a patient's brain, by observing which areas of the brain become active (by observing, for example, the blood oxygen level on the MRI) in response to stimulation of a particular area of the brain. Thus, the effect of stimulation of one part of the brain upon other parts of the brain can be observed and recorded in order to create a map of functional connectivity within the brain of normal subjects as well as the brains of subjects suffering from some psychiatric impairment such as depression or schizophrenia. Development of functional brain maps, that is relationships between activation of one area of the brain and the effect that activation of that area has on other areas of the brain, can significantly improve understanding of the operation of the brain in both normal subjects and those with any type of cognitive disorder.

The invention can also be used to identify pathway lesions or problems for any type of cognitive disorder by comparing, for example, the MRI of patients with a cognitive disorder with a normal MRI.

The invention can also be used to determine the efficacy of various treatments. For example, if the patient's brain was in an undesired state, TMS could be applied and the effect on the MRI (in particular, the effect on the blood oxygen level) could be monitored and the TMS could be applied until the MRI indicates that the patient's brain is no longer in an undesired state. That is, the blood oxygen levels or other parameters being monitored by the MRI are no longer abnormal. In the same way, the invention can be used to determine when a patient's brain has reached a desired state. For example, TMS can be applied and the MRI can be monitored and the treatment continued until the particular parameters being tracked, such as blood oxygen level, have reached a desired state in the MRI.

Furthermore, the invention can be used to make TMS applications more efficient. For example, if it is desired to stimulate a specific area of the brain, TMS can be applied, the MRI can be observed, and if the MRI indicates that a different region of the brain was activated rather than the target region, the position of probe 30 can be adjusted and the MRI observed once again. This process may be continued until probe 30 is stimulating the precise area of the brain that is desired.

In addition, the present invention allows the results of a TMS treatment to be seen immediately after stimulation. Thus, the immediate and longer term effects of TMS stimulation can be observed.

Having thus described at least one illustrative embodiment of the invention, various alterations, modifications, and improvements will readily occur to those skilled in the art. Such alterations, modifications, and improvements are intended to be within the spirit and scope of the invention. Accordingly, the foregoing description is by way of example only and is not intended as limiting. The invention is limited only as defined in the following claims and the equivalents thereto.

What is claimed is:

1. A method for monitoring a magnetic resonance image of a patient during administration of transcranial magnetic stimulation, comprising the steps of:
   applying transcranial magnetic stimulation (TMS) to a patient using a probe that is substantially constructed of non-ferromagnetic material;
   monitoring a magnetic resonance image (MRI) of a patient during application TMS;
   wherein application of the TMS is not synchronized with monitoring of the MRI.

2. The method of claim 1, wherein the step of applying TMS includes applying symmetrical biphasic stimulation.

3. The method of claim 1, wherein the TMS is applied and the MRI is monitored simultaneously.

4. The method of claim 1, wherein the step of applying transcranial magnetic stimulation (TMS) to the patient includes a step of applying the transcranial magnetic stimulation using a probe that, when connected to a conductor of a TMS device that administers the transcranial magnetic stimulation, is substantially constructed of non-ferromagnetic material.

5. A method for monitoring a magnetic resonance image of a patient during administration of transcranial magnetic stimulation, comprising the steps of:
   applying transcranial magnetic stimulation (TMS) to a patient using a probe that is substantially constructed of non-ferromagnetic material; and
   monitoring a magnetic resonance image (MRI) of the patient during TMS;
   wherein application of the TMS does not need to be synchronized to monitoring of the MRI; and
   wherein the method further comprises a step of controlling a torque resulting from interaction between a magnetic field produced by the TMS probe and a magnetic field produced by a system that provides the MRI.

6. The method of claim 5, wherein the step of controlling the torque includes locating a pad between the probe and the patient.

7. A method for monitoring a magnetic resonance image of a patient during administration of transcranial magnetic stimulation, comprising the steps of:
   applying transcranial magnetic stimulation (TMS) to a patient using a probe that is substantially constructed of non-ferromagnetic material; and
   monitoring a magnetic resonance image (MRI) of a patient during TMS;
   wherein application of the TMS does not need to be synchronized to monitoring of the MRI; and
   wherein the step of monitoring the MRI during TMS includes monitoring changes in a patient's blood oxygen level.

8. The method of claim 7, further comprising the step of determining a functional relationship between an area of a patient's brain subjected to TMS and another area of the brain by monitoring changes in blood oxygen level.

9. The method of claim 8, further comprising the step of repeating the determining step for a plurality of different areas of the patient's brain.

10. The method of claim 7, further comprising the step of monitoring the MRI of the patient and continuing applying TMS until the MRI of the patient is in a desired state.

11. The method of claim 7, further comprising the step of monitoring the MRI of the patient and continuing applying TMS until the MRI of the patient is no longer in an undesired state.

12. A system for monitoring a magnetic resonance image of a patient during administration of transcranial magnetic stimulation, comprising:
   a transcranial magnetic stimulation (TMS) device;
   a magnetic resonance imaging (MRI) system;
   a probe, coupled to the TMS device, the probe being constructed and arranged to deliver transcranial magnetic stimulation during operation of the MRI system, wherein the probe is substantially constructed of non-ferromagnetic material;
   whereby timing of operation of the TMS device is not synchronized with timing of operation of the MRI system.

13. The system of claim 12, wherein the TMS device provides symmetrical biphasic magnetic pulses.

14. The system of claim 12, wherein the probe applies a magnetic pulse simultaneously with the MRI system monitoring the magnetic resonance image of the patient.

15. The system of claim 12, further comprising a pad disposed between the probe and the patient.

16. The system of claim 12, further comprising a conductor that couples the probe to the TMS device, wherein the probe and interconnections that connect the probe to the conductor are substantially constructed of non-ferromagnetic material.

17. A system for monitoring a magnetic resonance image of a patient during administration of transcranial magnetic stimulation, comprising:
   a transcranial magnetic stimulation (TMS) device;
   a magnetic resonance imaging (MRI) system; and
   a probe, coupled to the TMS device, the probe being constructed and arranged to deliver transcranial magnetic stimulation, wherein the probe is substantially constructed of non-ferromagnetic material;
   wherein timing of operation of the TMS device does not need to be synchronized to timing of operation of the MRI system; and
   wherein the probe is disposed within an imaging coil of the MRI system.

* * * * *

UNITED STATES PATENT AND TRADEMARK OFFICE
CERTIFICATE OF CORRECTION

PATENT NO. : 6,198,958 B1
DATED : March 6, 2001
INVENTOR(S) : John R. Ives, Alvaro Pascual-Leone and Qun Chen It is certified that error appears in the above-identified patent and that said Letters Patent is hereby corrected as shown below:

<u>Column 5,</u>
Line 32 should read as follows:

patient during application of the TMS;

Signed and Sealed this

Seventh Day of August, 2001

*Attest:*

*Attesting Officer*

NICHOLAS P. GODICI
*Acting Director of the United States Patent and Trademark Office*